(12) United States Patent
Steyn

(10) Patent No.: US 6,468,249 B1
(45) Date of Patent: Oct. 22, 2002

(54) DEVICE FOR DRAWING BLOOD

(75) Inventor: Ricardo Sheath Oxford Steyn, Johannesburg (ZA)

(73) Assignee: Sleeping Dog Intellectual Property (Pty) Ltd. (ZA)

( * ) Notice: Subject to any disclaimer, the term of this patent is extended or adjusted under 35 U.S.C. 154(b) by 0 days.

(21) Appl. No.: 09/647,956

(22) PCT Filed: Mar. 31, 1999

(86) PCT No.: PCT/IB99/00556
§ 371 (c)(1),
(2), (4) Date: Nov. 21, 2000

(87) PCT Pub. No.: WO99/51290
PCT Pub. Date: Oct. 14, 1999

(30) Foreign Application Priority Data

Apr. 6, 1998 (ZA) ............................................. 98/2888

(51) Int. Cl.⁷ ............................................... A61M 5/32
(52) U.S. Cl. ........................................ 604/192; 604/198
(58) Field of Search ................................ 604/192, 195, 604/196, 198, 162, 164.08, 403, 411, 412, 413, 110

(56) References Cited

U.S. PATENT DOCUMENTS

| | | | | |
|---|---|---|---|---|
| 4,592,744 A | * | 6/1986 | Jagger et al. ................ | 604/192 |
| 4,927,414 A | * | 5/1990 | Kulli ........................... | 604/110 |
| 4,955,871 A | * | 9/1990 | Thomas ....................... | 604/217 |
| 5,002,536 A | * | 3/1991 | Thompson et al. .......... | 604/192 |
| RE33,585 E | * | 5/1991 | Haber et al. ................. | 604/198 |
| 5,209,739 A | * | 5/1993 | Talalay ........................ | 604/195 |
| 5,407,431 A | * | 4/1995 | Botich et al. ................ | 604/110 |
| 5,549,568 A | * | 8/1996 | Shields ........................ | 604/192 |
| 5,584,819 A | * | 12/1996 | Kopfer ........................ | 604/239 |
| 5,746,718 A | * | 5/1998 | Steyn .......................... | 604/192 |
| 5,817,070 A | * | 10/1998 | Tamaro ....................... | 604/263 |
| 6,159,185 A | * | 12/2000 | Tahihata ...................... | 604/198 |

* cited by examiner

Primary Examiner—Teresa Walberg
Assistant Examiner—Leonid Fastovsky
(74) Attorney, Agent, or Firm—Piper Rudnick; Michael L. Kenaga

(57) ABSTRACT

A device for drawing blood includes a disposable holder (12) defining a socket (14) for receiving one end of a vacuum vial (18). The holder (12) includes an inner needle-receiving formation (26) and an outer needle-receiving formation (28), the inner and outer needle-receiving formations being in fluid communication with one another. A hollow needle (32) is connected to the inner needle-receiving formation (26) so as to extend into the socket (14) for puncturing a stopper (52) on the vacuum vial when the vial is inserted into the socket. The outer needle-receiving formation (28) carries a hypodermic needle (38) and a safety cover (42) for the hypodermic needle. The safety cover includes a cup (44) having an off-centre opening (46) through which the point of the needle (38) can pass, and a resilient member (48) for holding the cup over the point of the needle when the needle is inoperative so as to cover the point of the needle.

7 Claims, 2 Drawing Sheets

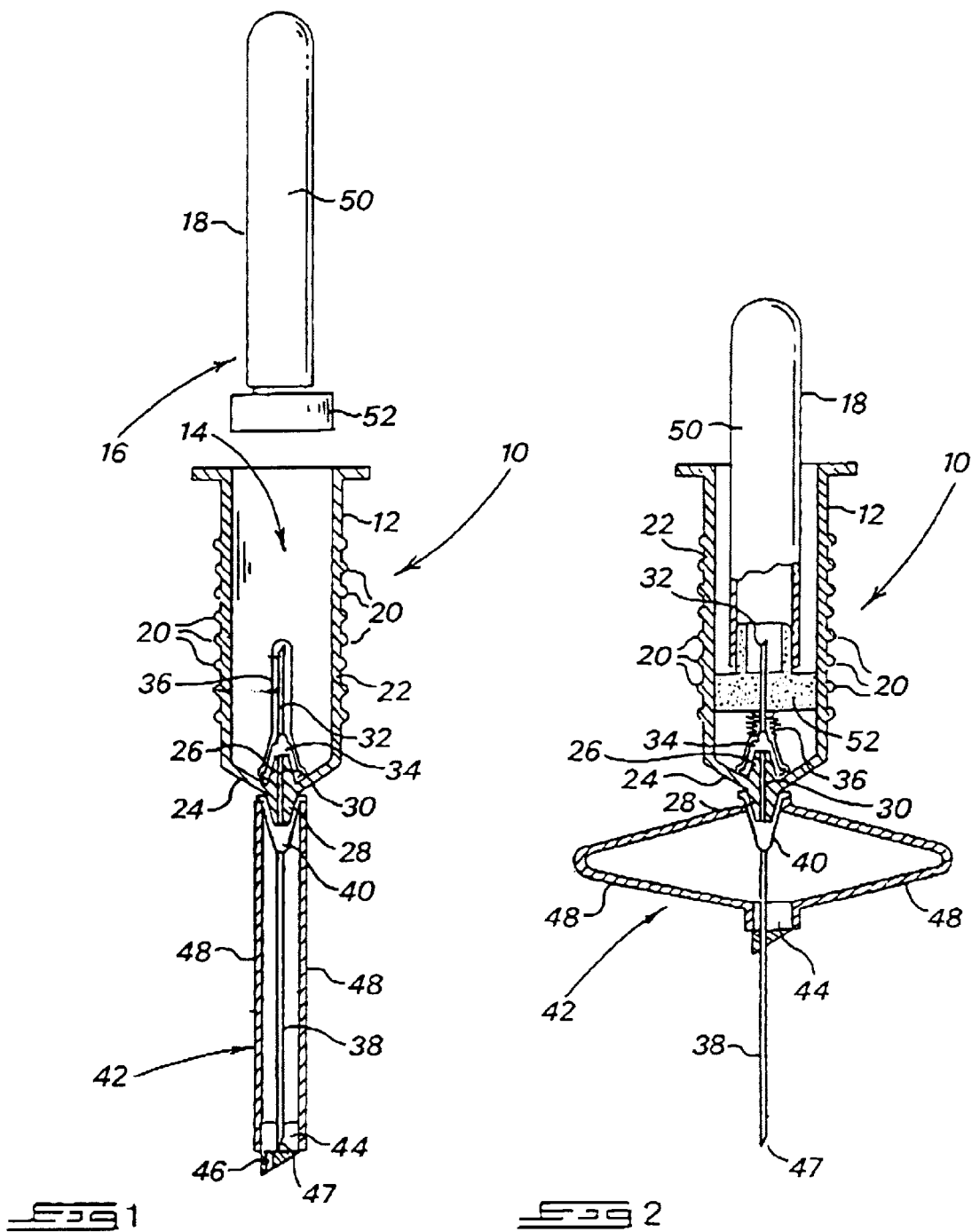

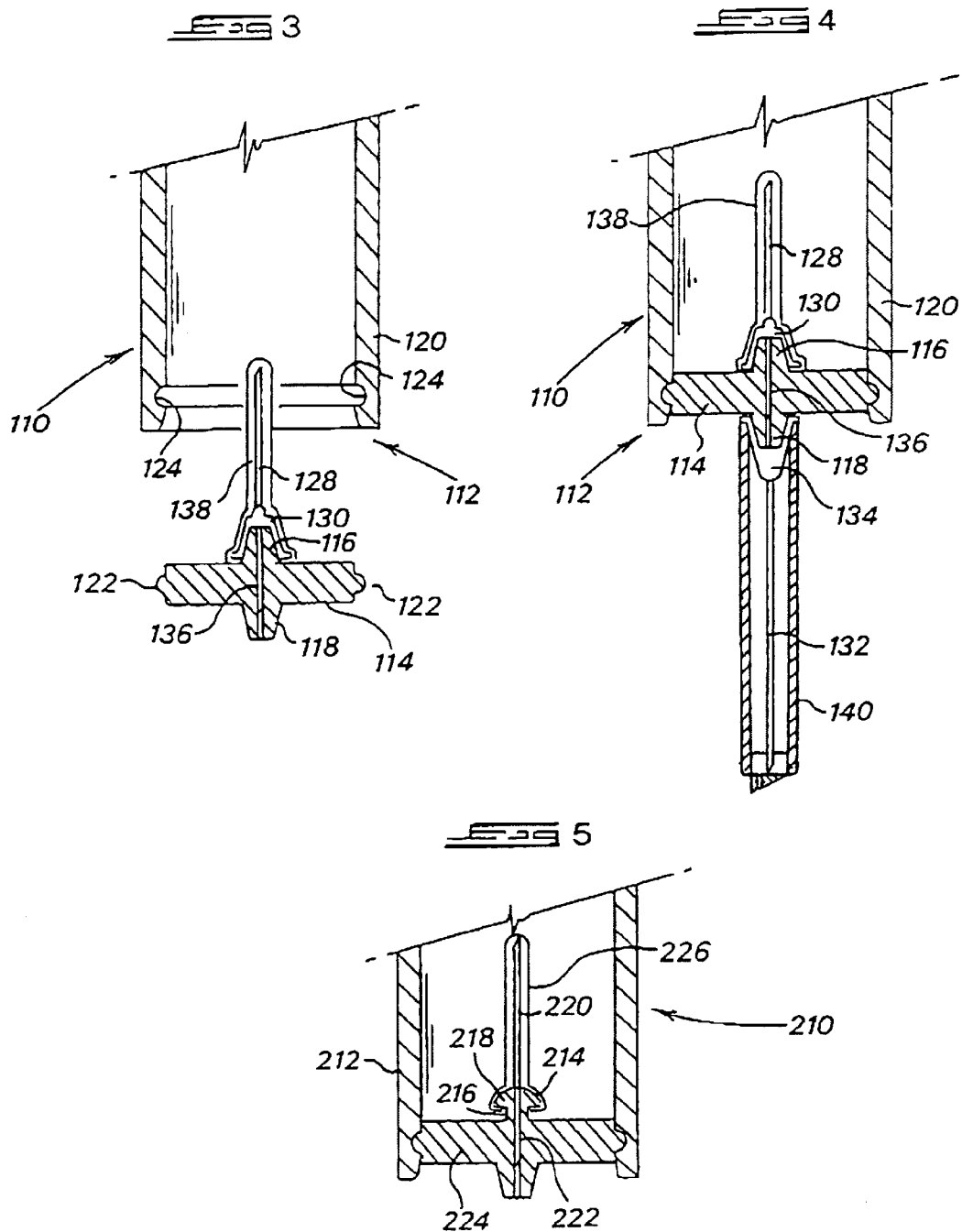

DEVICE FOR DRAWING BLOOD

BACKGROUND OF THE INVENTION

THIS invention relates to a device for drawing blood.

Conventional devices for drawing blood include a vial having a synthetic rubber stopper. The vial is supplied with a lower internal pressure than ambient pressure and is commonly referred to as a vacuum vial or a Vacutainer.

Generally, the vacuum vial is used in conjunction with a holder defining a socket for receiving the vial. The holder also defines an opening for receiving a needle arrangement having an inner, hollow needle which is arranged to extend into the socket and an outer, hypodermic needle which is arranged to extend outwardly from the holder, the inner and outer needles being connected so as to be in fluid communication with one another.

To draw blood, the point of the hypodermic needle is introduced into a patient's vein, and thereafter the vacuum vial is inserted into the holder socket so that the inner needle puncture the vial stopper. When this occurs, the pressure differential across the needle arrangement due to the relatively low pressure in the vacuum vial causes blood to be drawn through the needle arrangement and into the vial.

Various protective coverings for the hypodermic needle are available to protect users from needle stick injuries. For example, WO 91/08787 discloses a finger guard which is arranged to cover a hypodermic needle on a needle arrangement so that a user's hands are protected during connection of the needle arrangement to a holder or disconnection of the needle arrangement from the holder. U.S. Pat. No. 5,295,972 also discloses a finger guard for a hypodermic needle. In this case, the finger guard includes an end cap with an off-centre opening for preventing the point of the needle from inadvertently becoming exposed.

A problem associated with conventional devices for drawing blood is that the holder is used over and over again while the needle arrangement is used only once. Accordingly, each time blood is drawn from a patient, a needle arrangement has to be connected to a holder and subsequently disconnected from the holder. Apart from taking time, the disconnecting of the needle arrangement from the holder after drawing blood from a patient involves the risk of a needle stick injury even where a protective cover is used.

Furthermore, since the scan holder is used over and over again, it is possible for blood in one sample to be contaminated by blood from another sample.

SUMMARY OF THE INVENTION

According to the invention there is provided a device for drawing blood including:

a disposable holder which defines a socket for receiving one end of a vacuum vial and which includes an inner needle-receiving formation projecting into the holder and an outer needle-receiving formation projecting outwardly from the holder, the inner and outer needle-receiving formations being in fluid communication with one another, characterised in that the inner and outer needle-receiving formations are incorporated into the holder during manufacture so as to form a permanent part of the holder;

a hollow needle is connected to the inner needle-receiving formation so as to extend into the socket for puncturing a stopper on the vacuum vial when the vial is inserted into the socket;

a hypodermic needle is connected to the outer needle-receiving formation so as to extend outwardly from the holder; and a safety cover is provided for the hypodermic needle, the safety cover including a cup having an off-centre opening through which the point of the needle can pass, and a resilient member for holding the cup over the point of the needle when the needle is inoperative.

The resilient member of the safety cover may comprise two limbs which extend along the length of the hypodermic needle and which are arranged to bias the cup into a position in which it covers the point of the needle. In this case, the hypodermic needle can be expressed for use by threading the point of the needle through the off-centre opening in the cup and drawing the cup back over the needle. When the safety cover is released after use, the resilient limbs automatically carry the cup back into the position in which it covers the point of the needle.

In one embodiment of the invention, the inner and outer needle-receiving formations are formed integrally with the holder.

In another embodiment, the holder is formed from two parts and the needle-receiving formations are integral with only one of the parts.

The needle-receiving formations may be designed to form a friction fit with the needles.

Typically, at least one of the needles is connected to its needle-receiving formation by means of a Luer Slip or Luer lock attachment.

In a preferred form of the invention, a resilient, synthetic rubber sheath is arranged to cover the inner needle when this needle is inoperative.

The inner needle-receiving formation may include a bore for receiving a portion of the inner needs. In this case, the inner needle-receiving formation may have a head for engaging one end of the synthetic rubber sheath for covering the inner needle.

Preferably, the holder includes a series of gripping ribs on the outer surface thereof to facilitate the handling of the device.

BRIEF DESCRIPTION OF THE DRAWINGS

The invention will now be described in more detail, by way of example only, with reference to the accompanying drawings in which:

FIG. 1 shows a cross-sectional view of a device according to the present invention with a vacuum vial;

FIG. 2 shows a cross-sectional view similar to that of FIG. 1 with the vacuum vial inserted into the device of the invention;

FIG. 3 shows a cross-sectional view of a portion of a device according to another embodiment of the invention in an unassembled condition;

FIG. 4 shows a cross-sectional view similar to that of FIG. 3 with the device in an assembled condition; and FIG. 5 shows a cross-sectional view of a portion of a device according to a further embodiment of the invention.

DESCRIPTION OF THE PREFERRED EMBODIMENTS

FIGS. 1 and 2 of the drawings illustrate a first embodiment of a device 10 for drawing blood according to the present invention. The device 10 includes a disposable holder 12 which defines a socket 14 for receiving one end 16 of a vacuum vial 18. The holder 12 has a series of gripping ribs 20 on a side wall 22 thereof, and is formed from a transparent or translucent plastics material so as to allow a user to see through the side wall 22 and into the socket 14.

An end wall 24 of the holder carries an inner needle-receiving formation 26 which projects into the socket 14 and an outer needle-receiving formation 28 which projects outwardly from the holder, as shown. The formations 26 and 28 are formed integrally with the holder 12 and are seen in FIGS. 1 and 2 to taper inwardly as they extend away from the end wall 24. The holder 12 also includes a bore 30 which extends between the needle-receiving formations 26 and 28 so that these formations are in fluid communication with one another.

An inner, hollow needle 32 is connected to the inner needle-receiving formation 26 by means of a Luer Slip attachment 34 so as to be aligned with the bore 30 and to extend into the socket 14, as illustrated. A resilient, synthetic rubber sheath 36 is arranged to cover the needle 32 when this needle is inoperative. The sheath 36 extends over the Luer Slip attachment 34 and is anchored within the socket 14 by the Luer Slip attachment.

On the other side of the end wall 24 an outer, hypodermic needle 38 is attached to the outer needle-receiving formation 28 by means of a Luer Slip attachment 40. This needle 38 is also aligned with the bore 30 and is arranged to extend outwardly away from the holder 12, as shown.

A safety cover 42 is connected to the needle 38 to prevent needle stick injuries. Typically, the cover 42 is of the kind described in South African patent 93/5510 and includes a cup 44 defining an off-centre opening 46, and a pair of resilient limbs 48 connected at one end of the cup 44 and at the other end to the Luer Slip attachment 40. The limbs 48 are arranged to hold the cup 44 over the point 47 of the needle 38 when the needle is inoperative. In this condition (see FIG. 1) the point of the needle 38 and the opening 46 are not aligned with one another and the safety cover has to be manipulated in order to expose the point of the needle.

The vacuum vial 18 is conventional in nature and consists of a transparent tube 50 formed from glass or a plastics material and a synthetic rubber stopper 52 for sealing tube. In practice, these sort of vials are supplied with a lower internal pressure than ambient pressure.

To draw blood with the device 10, the hypodermic needle 38 is exposed and the point 47 of this needle is introduced into the blood stream of a patient. The needle 38 is exposed by aligning it with the opening 46 and then carefully threading the needle through the opening by drawing the cup 44 back over the needle into the position illustrated in FIG. 2. In this position, the resilient limbs 48 are flexed outwardly and bias the cup 44 back towards the FIG. 1 position. Accordingly, the safety cover 42 has to be held in the FIG. 2 position during use.

Thereafter, the vacuum vial 18 is inserted into the socket 14 as illustrated in FIG. 2. Initially, before the vacuum vial reaches the needle 32, the resilient sheath 36 covers the point of these needle and prevents blood from draining through this needle point. However, when the vacuum vial 18 is fully inserted into the socket 14, the needle 32 punctures the stopper 52 and the sheath 36 is driven away from the point of this needle by the stopper, thereby exposing the point of the needle. As soon as the needle 32 penetrates the stopper 52 and enters the vial 18, the pressure differential across the needles 32 and 38 causes blood in the patient's blood stream to be drawn through the needles and into the vial.

Once sufficient blood has been drawn, the vial 18 is removed from the socket 14 so that the blood can be tested.

As the vial is withdrawn from the socket, the resilient sheath 36 resumes its FIG. 1 position so as to cover the needle 32. Thereafter, the point 47 of the needle 38 is removed from the patient's blood stream, and when this occurs the resilient limbs 48 automatically move the cup 44 back into the position illustrated in FIG. 1. This reduces the likelihood of a needle stick injury after the hypodermic needle has contacted the patient's blood. With the point of the needle 38 covered, the entire device 10 is then disposed of.

FIGS. 3 and 4 illustrate a device 110 according to another embodiment of the invention. In this case, the holder 112 is formed in two parts which are joined together. In FIG. 3, the two parts are illustrated detached from one another prior to the final stage in the manufacturing process. As can be seen, one of the parts comprises an end wall 114 with integrally formed inner and outer needle-receiving formations 116 and 118, respectively, and the other part comprises a tubular housing 120. The end wall 114 carries a projecting formation 122 which is arranged to clip into a corresponding recess 124 in the inner face of the housing 120. FIG. 4 illustrates the end wall 114 and the housing 120 connected to one another to form the holder 112.

Apart from the two-part structure of the holder 112, the rest of the device is similar to the device 10 described above with reference to the first embodiment of the invention. Accordingly, the device 110 includes an inner needle 128 connected to the formation 116 by means of a Luer Slip attachment 130, an outer needle 132 connected to the formation 118 by means of a Luer Slip attachment 134, a bore 136 extending between the formations 116 and 118, a resilient sheath 138, and a safety cover 140 for the needle 132.

A third embodiment of a device 210 according to the invention is illustrated in FIG. 5. In this case, a holder 212 is formed as a two-part structure, as in the case of the second embodiment, but here an inner needle-receiving formation 214 has a neck 216 and a head 218, as shown. An inner needle 220 extends into a bore 222 in an end wall 224 so as to be firmly secured to the end wall. In this regard, the needle 220 may be arranged to form a friction fit with the bore 222 or it may be adhered to the side wall of the bore.

The head 218 is designed to form an anchor for a resilient sheath 226 so as to prevent this sheath from being withdrawn from the needle 220, in use. Apart from the differences described above, the rest of the device 210 is similar to the device 110 of the second embodiment of the invention.

It should be appreciated that various other configurations could be used to attach the needles to the holder. For example, instead of the Luer Slip attachment a Luer Lock attachment could be used.

An important feature of the invention is that the device includes a safety cover for the hypodermic needle which reduces the risk of a needle stick injury. In addition, the inner needle is secured to the holder when the device is supplied to a user and is designed to be disposed of with the holder. This avoids the need to connect the inner needle to the holder prior to use and to disconnect the needle from the holder after use. Apart from saving time, this further reduces the risk of a needle stick injury.

Furthermore, the device of the invention is designed to be disposed of without first removing the needles from the holder. Accordingly, unlike conventional devices, the holder is used only once. This avoids the possibility of one blood sample being contaminated by blood from another sample drawn with the same holder.

What is claimed is:

1. A device for drawing blood, comprising:

a disposable holder which defines a socket for receiving one end of a vacuum vial and which includes an inner needle-receiving formation projecting into the holder and an outer needle-receiving formation projecting outwardly from the holder, the inner and outer needle-receiving formations being in fluid communication with one another;

the inner and outer needle-receiving formations are incorporated into the holder during manufacture so as to form a permanent part of the holder;

a hollow needle is connected to the inner needle-receiving formation so as to extend into the socket for puncturing a stopper on the vacuum vial when the vial is inserted into the socket;

a hypodermic needle is connected to the outer needle-receiving formation so as to extend outwardly from the holder; and a safety cover is provided for the hypodermic needle, the safety cover including a cup having an off-center opening through which the point of the needle can pass, and a resilient member for holding the cup over the point of the needle when the needle is inoperative.

2. A device according to claim 1, wherein the resilient member of the safety cover comprises two limbs which extend along the length of the hypodermic needle and which are arranged to bias the cup into a position in which it covers the point of the needle.

3. A device according to claim 1, wherein the needle-receiving formations are designed to form a friction fit with the needles.

4. A device according to claim 3, wherein at least one of the needles is connected to its needle-receiving formation by means of a Luer Slip or a Luer Lock attachment.

5. A device according to claim 1, wherein the inner needle-receiving formation which includes a bore which is sized to receive a portion of the inner, hollow needle.

6. A device according to claim 1, comprising a resilient sheath which is provided for covering the inner, hollow needle when this needle is inoperative.

7. A device according to claim 1, wherein the holder includes a series of gripping ribs on the outer surface thereof to facilitate the handling of the device.

* * * * *